Figure 10:
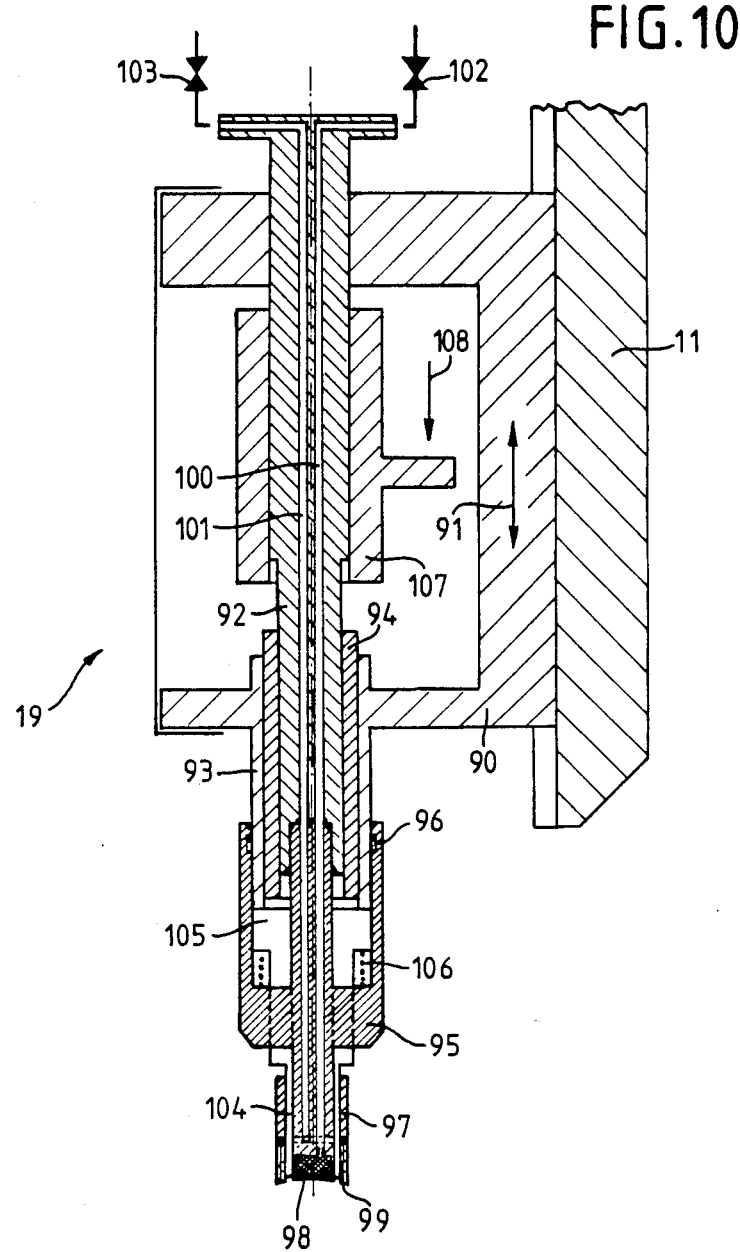

United States Patent [19]

Gründler

[11] Patent Number: 4,744,362
[45] Date of Patent: May 17, 1988

[54] DEVICE FOR TRANSPLANTING THE CORNEA OF THE HUMAN EYE

[76] Inventor: Patrik Gründler, Iddastrasse 7, CH-9098 St. Gallen, Switzerland

[21] Appl. No.: 878,894

[22] Filed: Jun. 26, 1986

[30] Foreign Application Priority Data

Jun. 27, 1985 [DE] Fed. Rep. of Germany ....... 3522998
Jun. 27, 1985 [DE] Fed. Rep. of Germany ....... 3522999
Jun. 27, 1985 [DE] Fed. Rep. of Germany ....... 3523015

[51] Int. Cl.⁴ .............................................. A61B 17/32
[52] U.S. Cl. ................................ 128/305; 128/303 R; 128/334 R
[58] Field of Search ................. 128/303 R, 305, 305.1, 128/310, 304, 334 R

[56] References Cited

U.S. PATENT DOCUMENTS

| 2,480,737 | 8/1949 | Jayle | 128/305 |
| 3,074,407 | 1/1963 | Moon et al. | 128/303 R |
| 4,205,682 | 6/1980 | Crock et al. | 128/305 |
| 4,429,696 | 2/1984 | Hanna | 128/305 |

FOREIGN PATENT DOCUMENTS 2854514 9/1979 Fed. Rep. of Germany ...... 128/305

Primary Examiner—Michael H. Thaler
Attorney, Agent, or Firm—Spencer & Frank

[57] ABSTRACT

A device for cornea operations on the human eye is composed according to the invention of various instruments and auxiliary implements in such a way that the transplantation of a disk-shaped part of the cornea (perforating keratoplasty) can very largely be carried out automatically by machine, surgical manipulations carried out by hand being almost eliminated. On a three-dimensionally adjustable carrier, an axis adjustment instrument (17), a trephine (18) and a transplanter (19) are fitted in such a way that these instruments can selectively be brought into coincidence with the visual axis of the patient and moved to a pre-adjustable height. Preferably, the carrier comprises an auxiliary carrier (8) and a rotary plate (11) which is pivotable about a horizontal axis (12) on this auxiliary carrier. This rotary plate carries the instruments. An eyeball holder ring (14) adjustable in height and a manipulator (15) as well as a cartridge changer (16) are immovably fitted to the auxiliary carrier (8). The instruments and auxiliary implements are described in detail. The device as a whole can be operated by means of a control panel (20). The functions and program sequences are electrically controlled, can be stored and are visually displayed on a monitor (21). (FIG. 1 for reference).

28 Claims, 7 Drawing Sheets

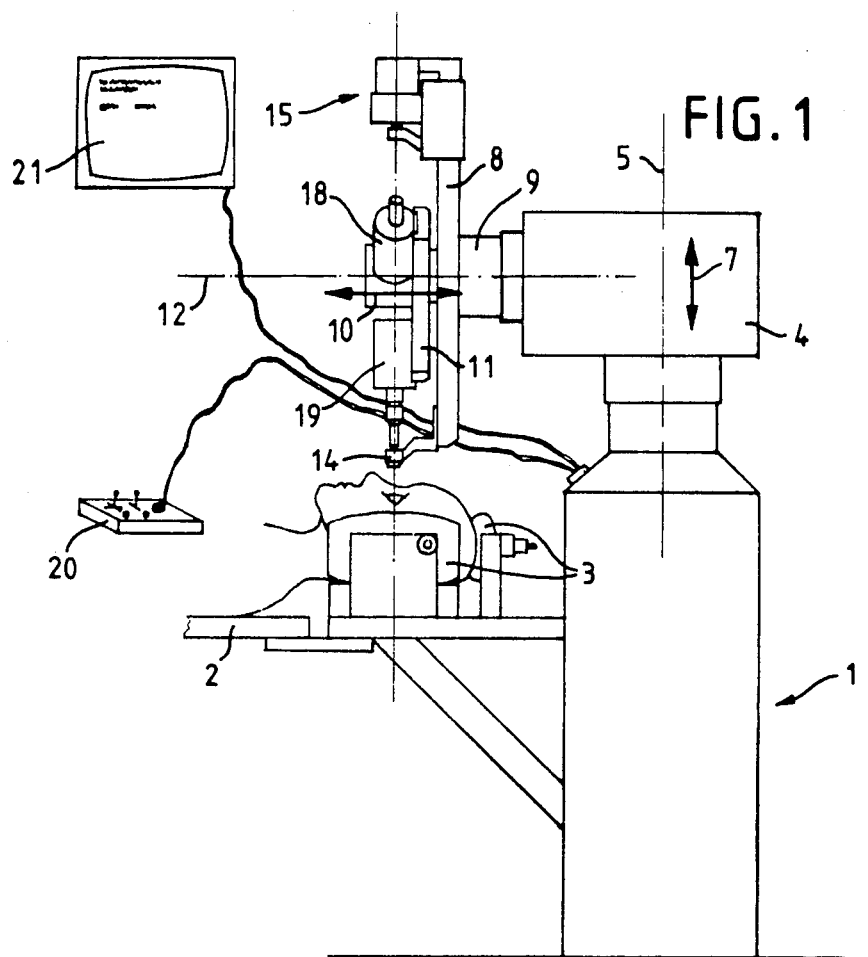
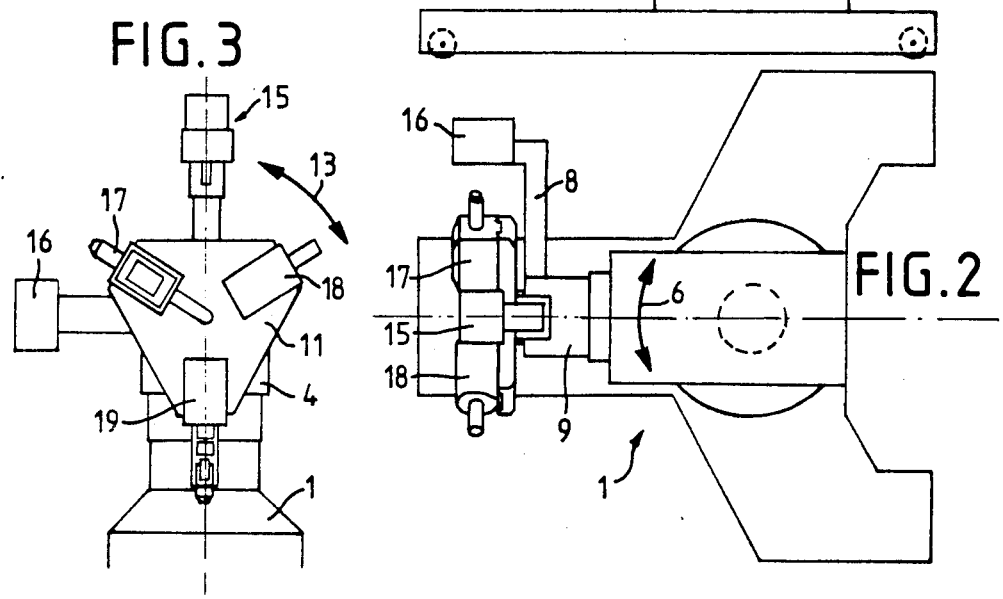

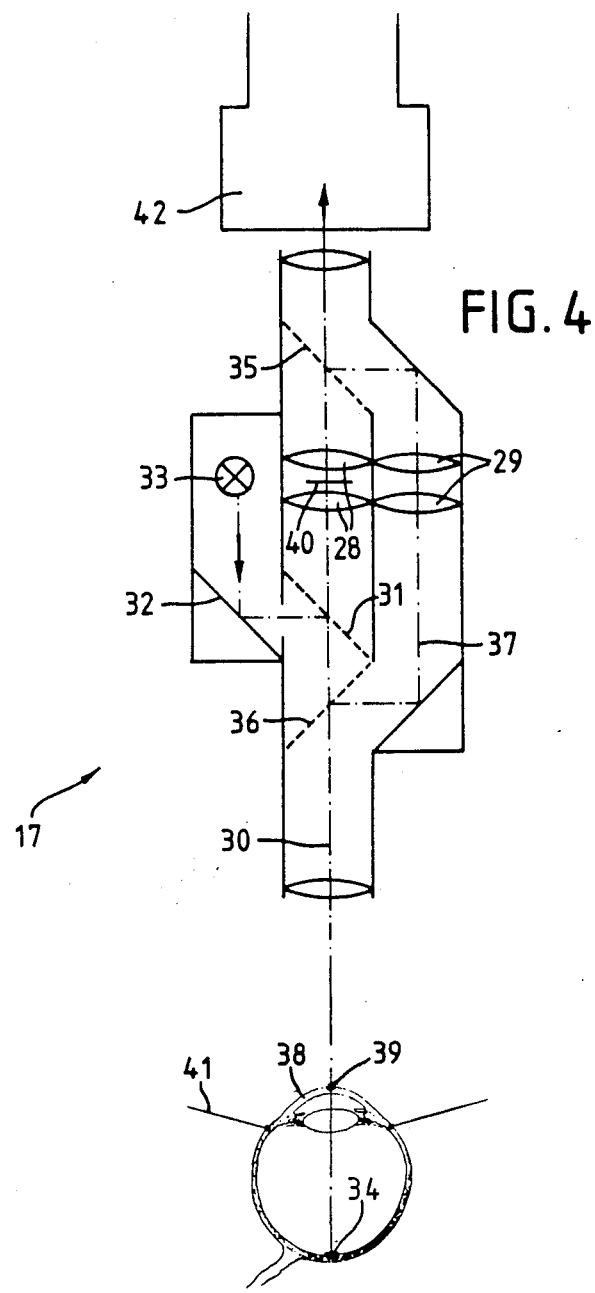

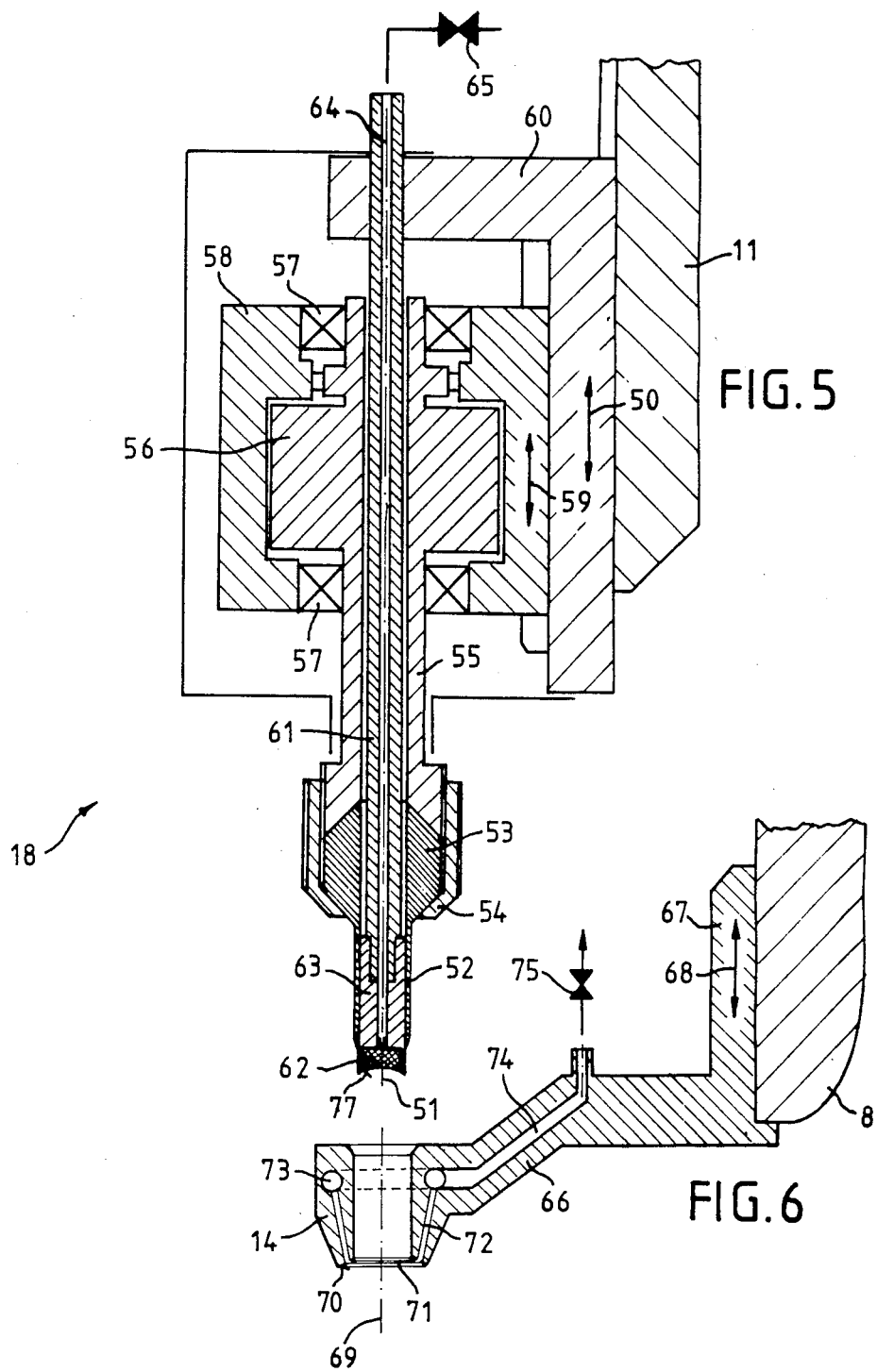

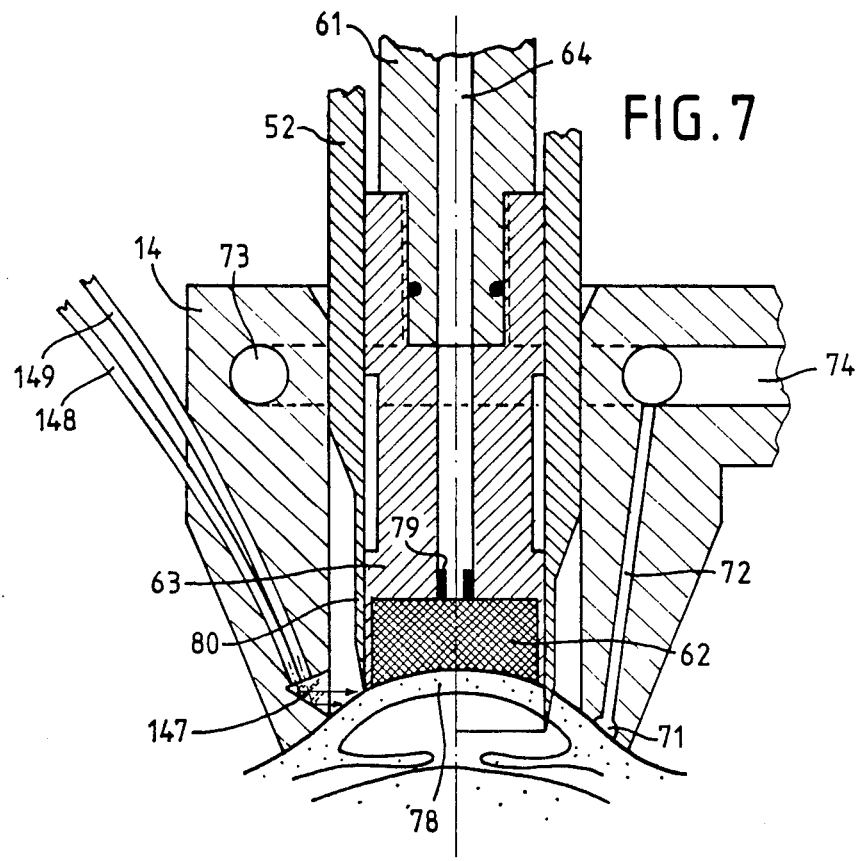
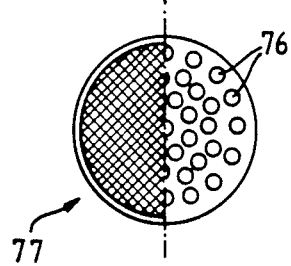
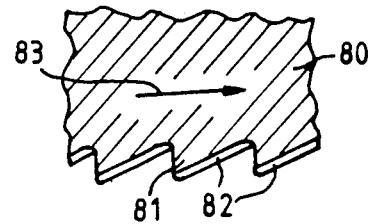

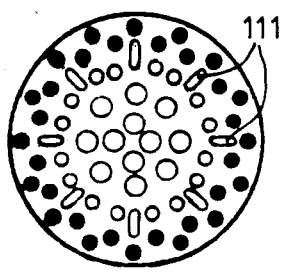
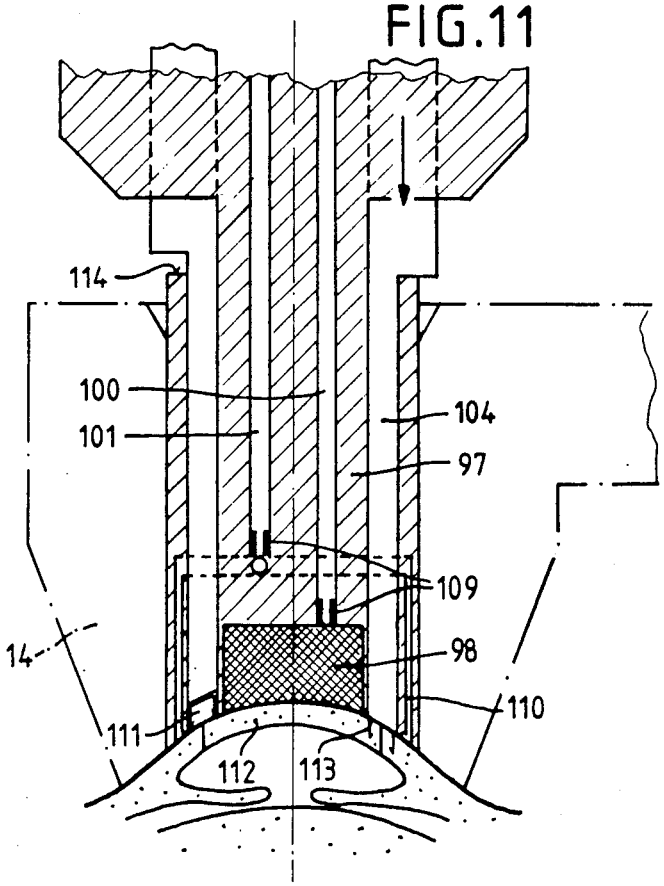
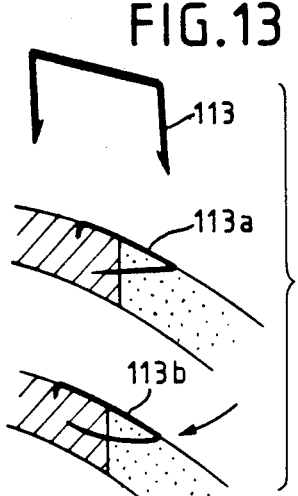
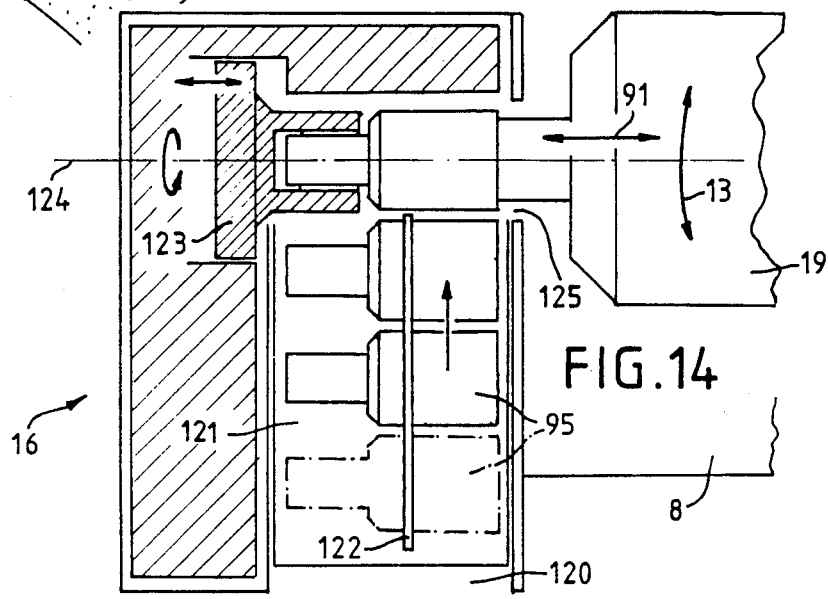

DEVICE FOR TRANSPLANTING THE CORNEA OF THE HUMAN EYE

The invention relates to a device for transplanting the cornea of the human eye.

Devices known from the patent literature are in each case intended or suitable only for carrying out defined steps or for solving part problems within the overall ophthalmo-surgical process. Particular reference is made to:

European patent application, publication No. 0,151,869, application date: Nov. 16, 1984. This describes an eyeball holder ring which can be fixed by suction and which is used for fixing the eye during the controlled photo-decomposition of certain zones of the cornea. However, this holder ring does not match the specific requirements of perforating keratoplasty.

U.S. Pat. No. 3,074,407, application date: Sept. 17, 1956. This describes a trephination device having a manually operated tubular cutter which passes through an annular gap between an inner suction pad and an outer suction pad and is axially guided with respect to these telescopic suction pads. The disadvantage of this device is that it cannot be centered relative to the optical axis of the eye with sufficient accuracy. When this trephination device is operated, there is a risk of injuring the internal structures of the eye, because the device is not fixed definitely relative to the head of the patient.

The current status of surgical technique in cornea transplantation can be described approximately as follows:

By means of a tubular cutter, which may be motor-driven, a circular incision is made by hand on the cornea and the previously delimited disk is then fully cut out and removed by hand by means of scissors and tweezers. The cornea disk which is to be transplanted is cut out by means of a punching tool or, again by hand without support, with scissors. Finally, the transplant is fixed in the eye of the recipient with needle and thread by means of fine sutures, likewise by hand without support.

Even though all these steps are carried out under an operating microscope, this procedure demands extraordinary dexterity, which only a very few experienced specialist surgeons possess. The duration of the operation is still several hours, even in the most favourable case.

No special devices have hitherto been used for manipulating the highly sensitive transplant, which has a diameter of about 8 mm. Rather, the transplant was gripped by means of tweezers. The resulting traumatization of the transplant delays healing and also leads to a less satisfactory result of the operation.

It is the object of the invention to propose a device which, as an integrated system, facilitates cornea transplantation on the human eye by logical and mutually matched interaction of its individual parts. Independently of the dexterity of the surgeon, a reproducible perfect result is to be achieved and, at the same time, the operating time is to be reduced considerably, for example down to 10 minutes.

The desired device should allow improved coincidence of the center axis of the plane of the cutting circle with the optical axis of the eye of the recipient and shorten the time for preparing the cornea of the recipient for transplantation.

It is a further object of the invention to fix a cornea disk, which has been removed and is held in position by apparatus means, rapidly and reliably and without deformations in the cornea of the recipient in such a way that it can rapidly take and heal, and the result of the operation should not depend on the manual dexterity of the surgeon.

A further object of the invention is to carry out the operation with such apparatus means that the transplant does not have to be gripped and moved by hand, for example by means of tweezers.

Finally, the invention has the object of designing the device in such a way that the parts which come into contact with the eye and the transplant can easily be taken off and sterilized, and are at a sufficient distance from the non-sterile parts.

Starting from the device described at the outset, these objects are achieved by the features comprised by claim 1. This device, with its instrument carrier movable in three dimensions, moves all the instruments under the supervision of the surgeon and by means of electronically controlled drives sensitively controlled by him. These movements are much more accurate than those which a man could carry out manually. Once one of the instruments has been set to the optical axis of the eye of the recipient, another instrument can also be moved into this position by pressing a button, since the positional co-ordinates can be stored. Another essential advantage is that the device can be programmed via a control unit (computer), so that the individual activities necessary during the operation can proceed automatically, under the control of the operator, so that it is possible to shorten the operation time to about ten minutes.

For constructional reasons, it is particularly advantageous to design the carrier as a rotary plate which is mounted about the horizontal axis and on which the instruments are mounted in a star-shaped arrangement with radial center axes. This rotary plate is mounted on an auxiliary carrier which, together with the rotary plate, is horizontally displaceable in the direction of the axis of the rotary plate, is rotatable about a vertical axis and is displaceable in height along this vertical axis. The auxiliary carrier thus executes the three-dimensional movement (height, radius and angle), whereas the rotary movement of the rotary plate merely serves to change the instruments between the eye of the recipient and the other components of the apparatus which are fixed to the auxiliary carrier.

The eyeball holder ring is mounted on the auxiliary carrier to be displaceable in the vertical direction and to be precisely adjustable, in such a way that the axis adjustment instrument, the trephine and the transplanter can be adjusted coaxially relative to the eyeball holder ring. The trephine and the transplanter are sensitively adjustable radially to the axis of the rotary plate and, with respect to their outer diameter, have such dimensions at the radially outer end that they can be inserted to fit into the orifice of the eyeball holder ring.

In order to make it easier to observe the progress of the operation, the eyeball holder ring can be made of a transparent material. However, light conductors or flexible optical fiber bundles can also have been inserted into the eyeball holder ring, penetrating the latter from the outside inwards. In this way, progress of the operation can be observed from the side of the front chamber under direct illumination.

Preferably, the manipulator which serves for holding the donor cornea and the transplant, for transferring the latter to the transplanter and for protecting the transplant between the individual steps of the operation, is also fitted to the auxiliary carrier. The manipulator can also have a device which allows wetting the transplant in the edge zone with a biocompatible adhesive (preferably fibrinogen). Finally, a clamp cartridge changer, which interacts with the clamp device of the transplanter, yet to be described, and supplies the latter automatically with new clamps for fixing the transplant, is fitted to the auxiliary carrier.

The axis adjustment instrument is in principle a monocular microscope with illumination for observing the fundus of the eye and has a marking which is visible in the ocular in the center of the visual field. Behind and in front of the lens system, semi-reflecting mirrors are provided, by means of which a part of the beam is branched off and added back to the main optical path, this second optical path running through a second lens system which produces a sharp image of the cornea surface. Before the operation, a small marking is made in the center of the cornea which is to be removed. Thereupon, the desired coincidence of the visual axis and of the optical axis of the axis adjustment instrument can be achieved by moving the instrument carrier, that is to say the auxiliary carrier and the rotary plate, in the horizontal in such a way, and by aligning the eye of the patient in such a way, that the visual field marking, the cornea marking and the macula lutea visible on the fundus are brought into coincidence. For the purpose of unhindered and rapid completion of the adjustment work, a video camera, which makes the adjustment process visible on a monitor, can be provided on the axis adjustment instrument.

A suitable trephine consists essentially of a holder and a shaft, to the end of which a suction pad having the shape of a molding of gas-permeable design is fixed, which molding has a contact surface approximating the outer surface shape of the human cornea. The shaft is surrounded by a tubular cutter which is preferably driven electrically and is displaceable and precisely adjustable relative to the shaft, in particular with respect to limiting the final depth of cutting. Such a simple trephine is to be preferred for the reason that it allows good visual control. Trephination is carried out in such a way that initially the suction pad is lowered until it is precisely placed upon the cornea surface, which is observable from the side, and the eyeball holder ring is then lowered by automatic comparison of positions down to the corresponding position, and the holder ring from then on holds the eyeball without pressure and deformation by aspiration of the corneal-scleral zone during the entire operation. The trephination can then be carried out automatically without any risk.

For better safeguarding against excessive vacuum or other incidents during trephination, it is proposed that the suction pad or its vacuum connection line should have a moisture-sensitive sensor which reduces the vacuum applied and triggers a signal, if chamber fluid is sucked up.

A particularly suitable tubular cutter, which exerts virtually no force on the cornea and gives a perfect cutting result, has, on its cutting edge, serrations with ground cutting facets which lead during the rotary movement.

According to the invention, the transplanter is used for inserting the transplant to fit into the cornea of the recipient and to fix it temporarily until the healing process is complete. The transplanter essentially consists of a holder which is able to carry out the same movements relative to the rotary plate as the trephine, of a shaft and of a suction pad located at the end of the shaft. The suction pad has, in contrast to that of the trephine, two zones, namely an inner zone and an outer annular zone surrounding the former, these zones being connected to vacuum sources which can be regulated separately. The inner zone of the suction pad grips the transplant and the annular zone grips the trephining edge which is to be joined to the transplant. In this connection, it should be noted that the outer diameter of this annular suction zone is located within the eyeball holder ring, since the transplanter can be introduced into the eyeball holder ring. The suction pad also comprises at least one clamp channel which merges into its contact surface, that is to say on the cornea, and in which a punch moves which ejects a clamp and thus presses it into the cornea. Preferably, several clamp channels are provided, the end orifices of which are arranged in a circle in the region between the annular zone and the inner zone. Preferably, the clamp channels extend in the longitudinal direction of the shaft, so that the projecting punches can be actuated together by means of a single impact element.

Since the force for pressing the clamps in must be smaller than the suction force of the suction pad, the number of clamps to be pressed in simultaneously is limited, also for constructional reasons. It is therefore proposed to introduce several sets of clamps in several steps with successive rotation of the suction pad about the transplanter axis, so that these sets have a regular circular arrangement in the finished state. For this purpose, and also to ensure sterilization, it is proposed that the foot part of the shaft, the suction pad and the punches form a clamp cartridge which is easily removable from the shaft by means of a quick-action coupling and can be selectively attached in different angular positions, the impact force being transmitted to the punches by means of a longitudinally movable sleeve. The quick-action coupling can be a bayonet closure for example.

The clamp cartridge changer which is fixed to the auxiliary carrier and has already been mentioned, automatically effects the removal of the empty clamp cartridge and the attachment of a new clamp cartridge. It contains a cavity into which a magazine pack with several sterilized clamp cartridges can be inserted. The magazine pack contains the clamp cartridges in the desired different angular orientations. A mechanical changing device with a longitudinally displaceable and rotatable gripper, which grips and rotates the clamp cartridges, is also provided, the new clamp cartridges being automatically supplied to the gripper and the empty cartridges being ejected. Once a clamp set has been pressed in, the transplanter moves out of the eyeball holder ring, after its vacuum lines have been disconnected, and, as a result of rotation of the rotary plate, moves into a position coaxially opposite to the clamp cartridge changer. Fitted with a new clamp cartridge, it then moves back and inserts these further clamps into the transplant or into the edge region of the cornea of the recipient.

Preferably, U-shaped clamps with a connecting bridge and two parallel arms are used, which have inward-pointing barbs on the arms. The arms can also be at an angle to the connecting bridge. The material used for the clamps can be a suitable plastic or metal. The cross-section can be flat, round or semi-circular. With other appropriate types of clamp apparatus, V-shaped clamps can also be used, in which case a barb is provided on only one arm. Such clamps are pressed into the connection point of the cornea of the recipient and the transplant, which is to be fixed, at a very acute angle relative to the cornea surface, so that one arm passes almost vertically through the cutting surfaces. This arm can also be bent in the form of a circle, in which case this clamp must be introduced by a rotary movement relative to the center of curvature of this arm. The second arm which is provided with barbs and rests on the outside of the cornea surface, as a result of the barb prevents the clamp from sliding out radially. This arm resting on the outside should be bent corresponding to the curvature of the cornea, so that the patient does not have the feeling of a foreign body being present.

The impact force is preferably generated electromagnetically or pneumatically. However, a spring, which is tensioned and triggered electromagnetically, or actuation by means of small explosive capsules can also be used as the impact force drive. In order to minimize shocks, it is proposed to transmit the impact force to the punches by means of a rod guided in the center of the shaft and hence to reduce the moving mass. On the other hand, a counter-weight can be provided which is coupled to the impulse-giving impact punch in such a way that it moves in the opposite direction to the latter and the impulses of the two masses are neutralized when they simultaneously strike their stops.

Finally, in order to avoid any contact of the transplant with a manually operated tool, the said manipulator is provided on the auxiliary carrier. It consists of a transplant gripper, a horizontally arranged cornea plate and a safety dish, which are mounted to be rotatable about a common vertical axis, and the safety dish, which contains a preserving fluid, for example physiological saline, is also movable up and down, so that the transplant gripper can partially dip into the fluid. The cornea plate has a central orifice, corresponding to the outer diameter of the trephine, and an annular support surface which surrounds the central orifice and which is formed as a gas-permeable suction zone and connected to a vacuum. The cornea plate serves as a support for the donor cornea with adhering tissue parts, the central region, which is to be cut out, being located above the orifice with its outside facing downwards. The transplant is cut out by the trephine coming from below. With the transplant lying on its suction pad, the trephine then moves upwards to the transplant gripper which has several pointed, corkscrew-shaped carrier elements which are in a star-shaped arrangement, move radially and into the cutting surfaces of the transplant and thus hold the latter, in order to then deposit it on the transplanter.

An illustrative embodiment of the invention is explained below by reference to the drawings, and the mode of action of the individual components is then illustrated in context by describing the course of the operation.

Figure 15:
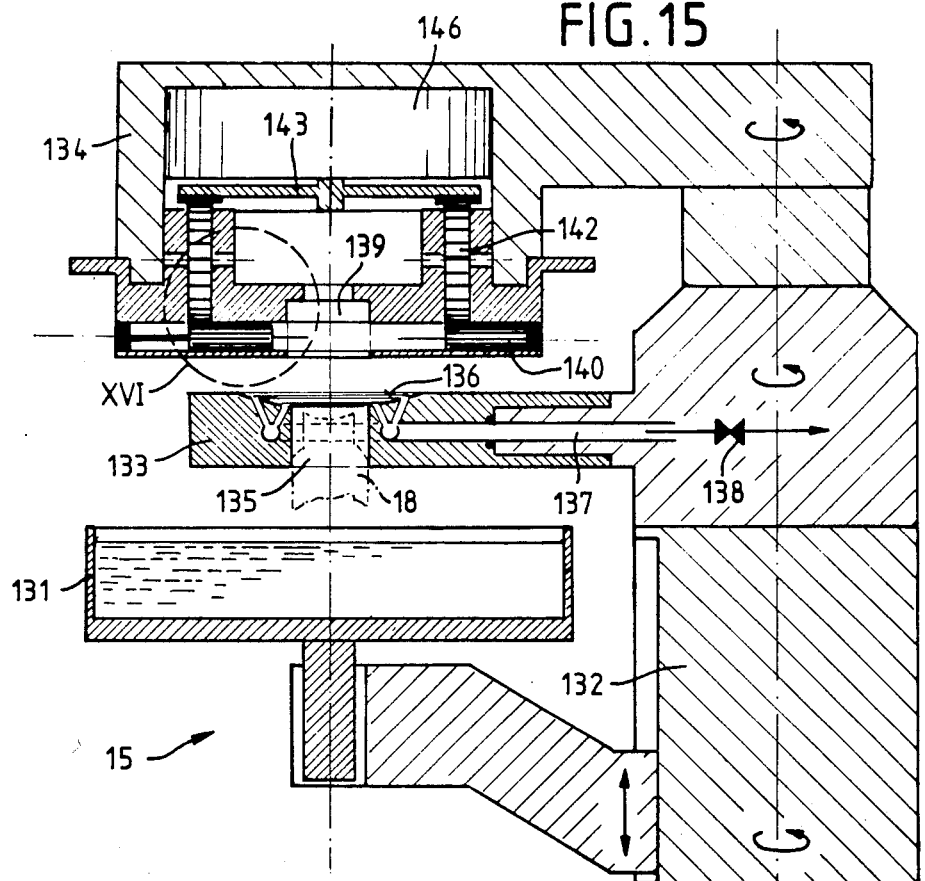
Figure 16:
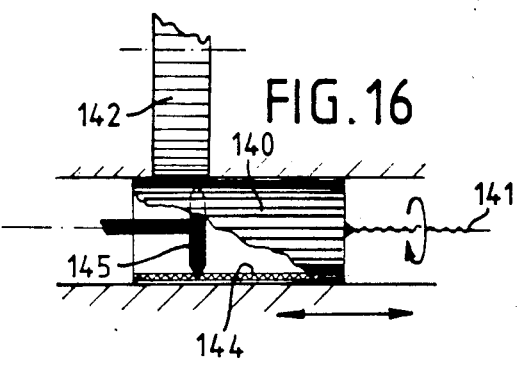

In detail:

FIG. 1 shows a side view of an integrated device for cornea transplanting, in a diagrammatic representation, FIG. 2 shows a plan view of the device according to FIG. 1, FIG. 3 shows a view of the rotary plate of the device according to FIG. 1, in the axial direction, FIG. 4 shows a diagrammatic axial section of an axis adjustment instrument, FIG. 5 shows an axial section of a motor-driven trephine, FIG. 6 shows an axial section of an eyeball holder ring, FIG. 7 shows an axial section of the eyeball holder ring with the trephine moved in, on a larger scale, FIG. 8 shows a view of the contact surface of the suction pad of the trephine in two embodiment variants, FIG. 9 shows a side view of a detail of the lower part of the tubular cutter, on an even larger scale, FIG. 10 shows an axial section of a transplanter with suction pad and clamping device, FIG. 11 shows an axial section of the lower part of the transplanter, on a larger scale, FIG. 12 shows a view of the support surface of another embodiment of the transplanter suction pad according to FIG. 11, FIG. 13 shows a view of various clamps, on a larger scale, FIG. 14 shows a diagrammatic representation of a clamp cartridge changer, FIG. 15 shows an axial section of a manipulator and FIG. 16 shows an enlarged detail XVI from FIG. 15.

The device according to FIGS. 1 to 3 comprises a base frame (1) which essentially consists of a movable base, a tower and a table bracket which is fixed to the tower and to which a patient carrier (2) is coupled. On the table bracket, there is a support with pressure pads (3) for fixing the head of the patient. In other respects, this fixing device can correspond to the devices used in stereotactic brain operations and can possess holding pins or the like.

In the tower, the rotating and lifting device is installed which rotates a tower head (4) relative to the vertical tower axis (5) in the direction of the arrow (6) (FIG. 2) and lifts and lowers it in the direction of the arrow (7). An auxiliary carrier (8) is horizontally displaceable in the tower head (4) in the direction of the arrow (10) by means of a sliding tube (9). This translational movement is also shared by a rotary plate (11) which is mounted in the auxiliary carrier (8) and the sliding tube (9) to be rotatable about a horizontal axis (12) in the direction of the arrow (13). The auxiliary carrier (8) can therefore not rotate and the rotary plate (11) cannot shift relative to the auxiliary carrier (8).

An eyeball holder ring (14) is fitted separately and adjustably in height to the bottom of a T-shaped auxiliary carrier (8). At the top, the auxiliary carrier (8) supports a manipulator (15), and a clamp cartridge changer (16) is fixed to the side arm of the auxiliary carrier. The rotary plate (11) carries three instruments, namely an axis adjustment instrument (17), a trephine (18) and a transplanter (19), in a star-shaped arrangement. The two last-mentioned instruments are radially adjustable relative to the axis (12) of the rotary plate (11).

All the abovementioned rotatary and translatory movements are controlled by high-precision electronic drives. Preferably, the positions can be digitally read off and stored, so that a position of a certain component, once fixed, can be retrieved after intervening movement. In particular, it is possible to adjust the rotary plate (11) into preferred angular positions in such a way that the individual instruments selectively assume a 6 o'clock, 9 o'clock or 12 o'clock position, these instruments pointing (in accordance with FIG. 3) downwards, to the left or upwards. By means of appropriate control programs, it is also possible to carry out a translational movement after a commanded rotary movement of the rotary plate (11), the desired end position having been determined beforehand by means of another instrument. The reference points for the translational movements of the individual instruments and of the eyeball holder ring (14) can likewise be adjusted and mutually matched.

A control panel (20) and a video monitor (21) which are connected to the device are available to the operator. The control panel essentially contains a control stick for common horizontal movement of the auxiliary carrier (8) and the rotary plate (11) in the directions (6 and 10), a switch for the lifting movement of the tower head (4) in the direction (7), preferably for two speeds, actuating elements for the individual instruments and the eyeball holder ring, and for the various programs. Finally, the control panel (20) also contains an emergency off button, the actuation of which ensures that air is admitted to all vacuum lines, motor movements stop and all components move upwards.

The axis adjustment instrument (17) according to FIG. 4 has a longer tube with a lens system (28) and a parallel shorter tube with a second lens system (29). In the straight-line main optical path (30), a semi-reflecting mirror (31) is arranged under 45°, by means of which the light from an illumination source (33) is introduced via a further mirror (32). This instrument, known to this extent, allows the fundus of the eye to be observed, and the magnification should be selected such that it is possible clearly to discern the outlines of the macula (34) in a sufficiently wide visual field.

Moreover, two further semi-reflecting mirrors (35 and 36) at right angles to one another are installed under 45° in the main optical path (30). By means of these mirrors, a parallel optical path (37) to the lens system (29) is created. By means of this lens system, which is of course separately adjustable, the surface of the cornea (38) and hence also the small marking (39) made beforehand in the center thereof can be observed in focus. Finally, a graticule (40) or a similar marking is provided in the main optical path. By axis-parallel adjustment of the axis adjustment instrument and by correction of the position of the eye of the patient, for example by manipulating two holding threads (41) fixed to the eyeball, the graticule (40), the marking (39) and the macula (34) can be made to coincide in the image.

In order to provide the surgeon with the necessary freedom of movement during this adjustment process, a video camera (42) is provided above the ocular or in place thereof. By means of this camera, the adjustment process can be observed on the monitor (21). It can be advantageous to use a so-called tubular camera and, for space reasons, to arrange this not in a straight-line extension of the instrument but in the horizontal sliding tube (9), in which case the optical path has to be deflected once.

The trephine shown in FIGS. 5 and 7 is mounted on the rotary plate (11), which is illustrated only in fragments, to be adjustable in the direction of the arrow (50) precisely parallel to the center axis (51) of the tubular cutter (52). At the upper end, the tubular cutter has an annular thickening (53) of trapezoidal cross-section and is connected by means of a knurled nut (54) to the hollow shaft (55) of the rotor (56) of an electric motor. The rotor is mounted by means of two bearings (57) in a stator (58) which is designed as a slide and can move in the direction of the arrow (59) relative to a holder (60), likewise precisely parallel to the axis (51) of the tubular cutter. The holder (60) in turn is - as mentioned - mounted displaceably on the rotary plate (11). The movement of the stator (58) relative to the holder (60) effects the vertical advance of the tubular cutter (52) during the cutting movement and amounts to only a few millimeters.

The holder (60) is rigidly connected to a shaft (61) which extends coaxially through the rotor (56) and the tubular cutter (52) and carries a cylindrical suction pad (62) at its lower end. The lower section (63) of the shaft with the suction pad (62) is connected to the shaft (61) by means of a screwed coupling. A central suction line (64) extends from the suction pad (62) through the shaft (61). At the top, it is connected via a valve (65) to a vacuum source. The outer diameter of the suction pad (62) and the inner diameter of the tubular cutter (52) are matched in such a way that the tubular cutter can rotate and shift in the axial direction, but the bearing play is kept as small as possible.

The eyeball holder ring (14) shown in FIG. 6 is connected via an arm (66) to a slide (67) which is movable in the direction of the arrow (68) relative to the auxiliary carrier (8), which is at a standstill during the operation, namely precisely parallel to the axis (69) of the bore in the eyeball holder ring. As FIG. 7 shows, the tubular cutter (52) fits precisely into this bore with the outer diameter of its middle section. The lower, so-called contact surface (70) of the conically downward-tapering eyeball holder ring (14) has a shallow, inward-rising conical shape. It has an annular narrow suction slot (71) which, via bores (72) running upwards, and an annular collecting channel (73), is connected to a suction line (74) which leads via a separate valve (75) to the vacuum source.

In FIG. 7, the eyeball holder ring (14) is shown on larger scale. The left-hand side of this figure shows a section of fiber-optic means of observation which are inserted into the ring in at least one position on the periphery. At this position, the suction slot (71) may be interrupted. A small optical prism (147) is located at the inner lower edge of the eyeball holder ring (14). A light conductor (148) and an optical fiber bundle (149), which latter is connected to a video camera, lead to that surface of this prism which points upwards to the left. The prism deflects the beams, emerging from the light conductor, towards the center of the ring, so that they pass through the corneal edge region and illuminate the operation field. With the monitor connected, progress of the operation can be observed through the fiber bundle (149).

FIGS. 7 to 9 also show further details of the active parts of the trephine. The suction pad (62), which is inserted into a thin-walled recess in the shaft section (3), is a porous molding in the example. The left-hand half of FIG. 8 likewise represents this embodiment. It would also be possible, however, for the suction pad to be a solid body penetrated by a multiplicity of suction bores (76) which end in its contact surface (77). This example is illustrated in the right-hand half of FIG. 8. The contact surface (77) is concave and, with respect to its curvature, matches the outer curvature of the cornea (78) as exactly as possible. In the immediate vicinity of the suction pad (62), a moisture sensor (79) is installed in the suction line (64), which sensor has the object of immediately detecting and signalling any chamber water which may have been aspirated after the trephination and, if necessary, automatically reducing or switching off the vacuum by means of the valve (65).

The longer middle section of the tubular cutter (52) bears against the cylindrical bore in the eyeball holder ring (14), so that these two components guide each other. The lower section (80) of the tubular cutter is made with extremely thin walls and is guided only from the inside by the shaft section (63), the outer surface of which bears against the tubular cutter. In the left-hand half of FIG. 7, the tubular cutter is in its retracted position of readiness. In the right-hand half, by contrast, the tubular cutter has been moved out up to complete severing of the cornea. The little cornea disk which has been cut out is suspended from the suction pad and is taken along when the trephine is moved up.

FIG. 9 shows an enlargement of the cutting edge of the tubular cutter section (80). Cutting facets (82) are ground on the flanks of the sawtooth-shaped serrations (81). The direction of rotation of the tubular cutter is selected such that the cutting edge shown moves in the direction of the arrow (83).

FIGS. 10 to 13 show the transplanter (19) with the clamp device attached thereto. The complete device according to FIG. 10 comprises a holder (90) which is fitted to the rotary plate (11) to be displaceable in the direction of the arrow (91). The direction of displacement runs parallel to the axial direction of a shaft (92) which is rigidly joined to the holder (90). The shaft penetrates a sleeve (93) which is molded to the holder (90) and projects downwards. Between the sleeve (93) and the shaft (92), there is an impact sleeve (94) which is loosely movable in the longitudinal direction.

A clamp cartridge (95) is slipped by means of a bayonet closure (96) from below over the sleeve (93). The bayonet closure has at least six pins distributed over the periphery, so that the clamp cartridge can be attached in three different angular positions, as desired. A cylindrical attachment (97) at the lower end of the clamp cartridge also fits into the bore of the eyeball holder ring (14). In view of the purpose of the clamp cartridge of firmly holding both the disk-shaped transplant, which is to be inserted into the cornea of the recipient, and the edge of the cut-out cornea of the recipient in the correct positions and mutually connecting them by clamps, the attachment (97) has two separate suction devices, namely a central suction pad (98) and a suction ring (99) surrounding the former. They are each connected to separate suction lines (100) and (101) which extend through the shaft (92) and are connected via valves (102 and 103) to the vacuum source.

The suction lines also run through the clamp cartridge, namely through a central, upward-pointing core which fits into a recess on the end face of the shaft (92) and thus makes a tight connection for the suction line sections.

In the annular zone between the two suction arrangements, eight clamp channels, which are filled by longitudinally movable punches (104) fitting into them, extend in the attachment (97) in the longitudinal direction. The punches have wider middle sections which extend through correspondingly enlarged channels in the middle region of the clamp cartridge (95) and at the top have an end section (105) which is once again widened. Small compression springs (106) hold the punches in an upper rest position. In the example, the force for driving the clamps in comes from a drive ring (107) which is displaceably mounted on the shaft (92) and, by means of its electromagnetic drive (not shown) or the like, moves downwards in the direction of the arrow (108) and takes the impact sleeve (94) along. The lower end of the latter comes to lie against the end sections (105) of the punches and thus also moves these downwards together.

FIG. 11 shows further details of the transplanter. The inner suction pad (98) is a porous body. At the start of the suction line (100), there is again a moisture sensor (109). The suction ring (99) consists of a multiplicity of suction channels (110) which pass in the longitudinal direction through the outer region of the attachment (97) and lead via a ring main to the suction line (101). FIG. 12 shows a view of the complete suction arrangement from below, suction channels of round cross-section also being used in the central region, as an alternative and in contrast to FIG. 11. FIG. 12 also shows the elongate cross-section and the star-shaped arrangement of the eight clamp channels (111). The essential point is that suction channels are provided also between the clamp channel orifices so that, in these regions, the transplant (112) and the cornea of the recipient, surrounding the transplant, are cleanly held right up to the edges. To simplify the illustration, the orifices of the suction channels (110) of the outer suction ring are shown as solid black dots, and the remaining suction orifices are shown as circles. In the innermost region, the suction orifices are slightly larger. Suction arrangements surrounding orifices of the clamp channels (111) can also be accomplished by means of spongy gas-permeable bodies.

One of the clamps (113) used in the example is shown in FIG. 13 on a greatly enlarged scale. It consists of two parallel arms and an inclined bridge. Barbs are fitted to the inside of the arms. The clamp is made of a suitable plastic and has a semi-circular cross-section.

FIG. 13 also shows a V-shaped clamp (113a). One arm, which is slightly shorter, is straight and the other, slightly longer arm is slightly curved corresponding to the surface curvature of the cornea. An inward-pointing tip (hook) is located at the end of this latter arm. This clamp (113a) is inserted in such a way that the straight shorter arm radially penetrates the lateral cutting surface and the slightly curved arm rests on the cornea surface, the tip penetrating into the surface. A further clamp (113b) differs from that just described by the first arm, which has no barb, having a circular curvature. Accordingly, it must be introduced on a circular path relative to its center of curvature.

In the left-hand part of FIG. 11, the punch (104) is shown in the rest position. Its lower end is slightly retracted relative to the orifice of the clamp channel, so that there is room in the clamp channel (111) for a clamp (113) with the bridge bearing against the likewise chamfered end face of the punch (104). Thus, at the start of the clamping step or in the case of the clamp cartridges held as stock, all eight clamp channels are loaded with one clamp each. Upon a signal, the drive ring (107) pushes all the punches downwards together, so that these press their clamps (113) into the tissue, as shown in the right-hand half of FIG. 11. The stop surface formed at the transition to the first widening of the punches then strikes the upper end face (114) of the attachment (97), whereby the punch movement is precisely limited. The length of the clamp arms is preferably less than the thickness of the transplant.

If eight clamps do not suffice for fixing the transplant, a further eight clamps each time can be fitted at angular offsets in further separate steps, so that the number of the clamps set in total can be increased as desired. This procedure is important also when, because of design considerations, the individual clamp cartridges have fewer clamp channels, for example only three. Only such a number of channels is necessary that, after the first clamping step, the transplant does not change its position temporarily and under the conditions of the operation. The ratio of suction force to punch force can set an upper limit to the number of clamps which can be introduced simultaneously.

FIG. 14 shows a clamp cartridge changer (16) which is fixed to the auxiliary carrier (8) and can receive a sterile magazine pack (121) in a cavity (120). This pack contains three clamp cartridges (95) in angular positions which differ by 15°; this is ensured by guide strips (122) in interaction with a corresponding external shape of the clamp cartridges. In the device, a rotary chuck (123) is also provided which can be rotated relative to its axis (124), which is horizontal in the example, and displaced. The cavity (120) has an orifice (125) in the direction of the axis (124).

The changing step proceeds as follows: the transplanter (19) is brought into the 9 o'clock position by pivoting the rotary plate (11). The arrangement is made such that the transplanter axis is then aligned with the axis (124). By displacing the transplanter in the direction of the arrow (91) on the rotary plate, the clamp cartridge is introduced through the cavity orifice (125) into the changer. The rotary chuck (123) then comes from the left, grips the clamp cartridge and turns the bayonet closure open. The transplanter is then retracted slightly and the empty clamp cartridge is ejected to the side by the rotary chuck. The topmost of the replacement cartridges then moves upwards, retaining its angular position, and takes the place of the ejected cartridge. The transplanter moves in again and the chuck puts the new cartridge in position. The transplanter with the new cartridge then moves out in the direction of the arrow (91) and pivots back into the 6 o'clock position.

Finally, FIG. 15 shows the manipulator (15) fixed to the top of the auxiliary carrier (8). It consists of three components pivotable about the same vertical axis (130), namely (from the bottom to the top) a safety dish (131) which is filled with physiological saline and which can be moved up and down on a hub (132), a cornea plate (133) and a transplant gripper (134). A vertical cylindrical bore (135) in the cornea plate (133) has the same diameter as the bore of the eyeball holder ring (14) and is arranged such that the trephine (80), indicated by dots and dashes, can move from below into its 12 o'clock position. At this time, the safety dish (131) must of course have been pivoted out of the way. The region around the bore (135) on the cornea plate is designed as an annular suction zone (136) for placing the donor cornea. The suction zone has a concave curvature corresponding to the form of the cornea and has two annular slots which are connected via a suction line (137) and a valve (138) to a vacuum source.

When in the appropriate angular position, the transplant gripper has a receiving orifice (139) on its underside coaxially above the bore (135) in the cornea plate. This orifice is surrounded by several gripper rolls (140) in a star-shaped arrangement, which carry needles (141) which point towards the common center and which, as can be seen from the detail according to FIG. 16, have the form of a fine corkscrew. The gripper rolls (140) have external toothing and are in engagement with intermediate gears (142) which are driven via a common sunwheel (143) by a motor. In addition, the gripper rolls (140) have an internal thread (144) in which the tips of a fixed T-piece (145) engage. Thus, when the gripper rolls are driven, they execute a translatory movement in their housing, following the thread (144), in such a way that all the needles (141) simultaneously move towards the center and are turned laterally into the transplant or are retracted. The transplant gripper is of such dimensions that, by pushing the safety dish (131) upwards, its lower part, in which the suspended transplant is located, can be immersed into the preserving fluid.

Overall, the operation proceeds as follows:

In preparation, the center of the cornea of the recipient must be marked. This is preferably done at a separate session, for example on the day before the operation. The auxiliary instrument used is a slit lamp attachment, in which the surgeon can see a group of concentric circles and a graticule. This circular template can be concentrically adjusted to the circular transition zone between the transparent cornea and the opaque connecting tissue. As the marking of the cornea center, a small colored dot or the like can be applied under local anaesthesia.

As a further preparation, the transplant can be obtained and made ready. For this purpose, the donor cornea is placed upon the cornea plate (133), with the epithelium facing downwards, and centered relative to the bore (135) by means of a mirror or the axis adjustment instrument (17) which has been moved into the 12 o'clock position, that is to say also with the aid of the monitor (21). With appropriate programming, the working steps automatically carried out by the device then follow:

the vacuum of the suction zone (136) is switched on;

the trephine (18) moves into the 12 o'clock position and from below into the bore in the cornea plate (133);

the trephining vacuum is switched on;

the tubular cutter (52) starts and carries out its cutting movement;

the trephine with the transplant moves even higher up (direction of the arrow 50) into the receiving orifice (139) of the transplant gripper;

the motor of the latter starts and the needles (141) are turned radially in the cutting surface of the transplant;

the suction head of the trephine is vented and the trephine moves downwards out of the bore in the cornea plate and further downwards;

the cornea plate (133) is pivoted out of the way;

the safety dish (131) is pivoted in and raised, so that the transplant is immersed in the preserving fluid and is thus secured for the time being;

the transplant preparation is verified on the monitor and the device is released for the operation.

For immediate preparation of the operation, the patient is laid on the carrier (2), and his head is fixed as carefully as possible and immovably with the aid of the pressure pads (3) or the holding pins. This is followed by anaesthesia and fitting of the holding threads (41) (FIG. 4) to the eyeball. The device is then coarsely aligned as to height and in the horizontal, that is to say in the directions of the arrows (7, 6 and 10). As a result, the axis adjustment instrument (17), which is in the 6 o'clock position, comes above the eye of the patient and roughly into the visual axis. This is followed by fine adjustment of the eyeball by means of the holding threads, with simultaneous fine adjustment of the axis adjustment instrument in the horizontal at a very much lower adjustment speed, until finally the graticule, the mark on the cornea center and the macula visibly coincide on the monitor.

After a program button has been pressed, the rotary plate (11) pivots until the trephine (18) has reached the six o'clock position. The adjustment movement (50) of the trephine (18) is then released. The operator lowers the trephine, and the latter first moves into the eyeball holder ring (14) and finally, penetrating the latter, approaches the cornea.

The operator carefully lowers the trephine further, until the suction pad (62) makes contact with the cornea of the patient; this can be accurately observed from the side. Then, the program button for the further automatic steps is pressed:

the height co-ordinate reached is stored;

in accordance with the latter, the eyeball holder ring (14) moves down relative to the auxiliary carrier (8) precisely to the height corresponding to the trephine, so that the contact surface (70) of the eyeball holder ring is also precisely seated, as shown in FIG. 7;

the vacuum of the suction pad (62) and of the suction slot (71) is switched on;

the next operation step is indicated on the monitor and can be started by the operator by means of the program key.

The operator presses the program button once more and thus starts the automatic trephination and subsequent transplantation, in detail as follows:

trephination of the cornea of the patient;

the depth of cutting has been set and fixed beforehand;

the trephine (18) with the cornea (78) of the patient suspended thereon moves up;

the eyeball holder ring remains unchanged;

the safety dish (131) is lowered and pivoted out of the way to the side;

the rotary plate (11) pivots the transplanter (19) into the 12 o'clock position;

the transplanter moves up into the receiving orifice (139) of the transplant gripper (134) and comes into contact with the transplant;

vacuum is applied to the inner suction pad (98) of the transplanter;

the transplant gripper (134) drives the gripper rolls (140) with the needles (141) radially outwards, so that the latter release the transplant;

the transplanter is retracted downwards, is rotated into the 6 o'clock position and moves into the eyeball holder ring (14);

the transplanter is lowered to the stored height co-ordinate, so that the transplant (112) will fit precisely into the cornea of the recipient;

the vacuum of the outer suction ring (99) of the transplanter is switched on and the trephination edge is thus also fixed;

the eight clamps (113) contained in the clamp cartridge (95) are inserted in the direction of the arrow (108) (FIG. 10) by switching on the impact drive;

all the vacuum in the transplanter is switched off (the two separate suction lines 100 and 101).

The actual operation has thus been concluded. If further clamps are still required, two further clamping steps take place as follows:

the transplanter (19) moves upwards out of the eyeball holder ring;

the transplanter pivots into the 9 o'clock position and moves into the clamp cartridge changer (16);

in the latter, the clamp cartridge (95) is taken off and a replacement cartridge is attached in an angular position changed by 15°;

the transplanter (19) moves back and pivots again into the 6 o'clock position;

it moves into the eyeball holder ring (14) and is again lowered until it comes into contact with the transplant and the cornea of the recipient. The vacuum of both suction zones is switched on again;

the second ring of clamps is inserted in an angular position offset by 15°;

this is then followed by the third clamping step in the identical order of individual steps;

the vacuum of the eyeball holder ring (14) is switched off;

the tower head (4) with all the components borne by it, including the eyeball holder ring, moves upwards and pivots away to the side by 90°;

"End of operation" indicated on the monitor.

I claim:

1. In a device for transplanting the cornea of the human eye, which device includes a base frame (1) constructed as a patient carrier, a head rest with a fixing structure (3) and an eyeball holder ring (14) which can be fixed during the operation and which can be placed with its lower surface (70), to which suction can be applied, upon the corneal-scleral transition zone of the eye, the improvement wherein said device further comprises:

a carrier (11) which is three-dimensionally adjustable by means of electonically controllable drives, said carrier being mounted on said base frame (1);

at least three instruments mounted on said carrier (11), including an optical axis adjustment instrument (17) for simultaneous monocular observation of the surface of the cornea and of the fundus of the eye of the patient, a trephine (18) for cutting out a circular disk-shaped central part of the cornea, and a transplanter (19) for transferring a cornea transplant (112) and fixing it in the eye of the patient; and means for storing the positional data of the instruments, and an electronic control systen operably connected to said carrier for adjusting said carrier (11) and said instruments such that an instrument which is to be selected moves on command into the position previously taken up by another instrument.

2. A device as claimed in claim 1, wherein the carrier is a rotary plate (11) which is mounted to be rotatable about a horizontal axis (12) and on which the instruments are mounted in a star-shaped arrangement which radial center axes.

3. A device as claimed in claim 2, wherein the rotary plate (11) is mounted in an auxiliary carrier (8) which, together with the rotary plate (11), is horizontally displaceable in the direction of the axis (12), is rotatable (6) about a vertical axis (5) and is displaceable in height (7) along the direction of this vertical axis (5).

4. A device as claimed in claim 3, wherein a manipulator (15) for holding the donor cornea and the transplant (112) and for transferring the transplant to the transplanter (19) is fitted to the auxiliary carrier (8).

5. A device as claimed in claim 4, wherein the maipulator (15) comprises a transplant gripper (134), a horizontally arranged cornea plate (133) and a safety dish (131), which are mounted to be rotatable about a common vertical axis (130), the safety dish (131) which contains a preserving fluid also being adjustable in height, so that the transplant gripper (134) can be partially immersed in the fluid.

6. A device as claimed in claim 5, wherein the cornea plate (133) has a central orifice (135) corresponding to the outer diameter of the trephine (18) and an annular contact surface (136) which surrounds this orifice and has a concave shape approximating the surface shape of the sclera parts, close to the cornea, of the human bulbus oculi and is designed as a gas-permeable suction zone and connected to a vacuum.

7. A device as claimed in claim 6, wherein the transplant gripper (134) has several needle-type carrier elements (141) which are in a star-shaped arrangement with their tips pointing towards the center of the star and which can radially move together by means of an appropriate drive arrangement (140 to 143) and penetrate the transplant (112) on its cutting surface.

8. A device as claimed in claim 3, wherein an automatic clamp cartridge changer (16) for removing an empty clamp cartridge (95) from a clamp device of the transplanter (19) and for attaching a new clamp cartridge is fitted to the auxiliary carrier (8).

9. A device as claimed in claim 8, wherein the clamp cartridge changer (16) contains, in a magazine cavity (120), several clamp cartridges loaded with clamps and attaches these cartridges one after the other in different angular orientations to the sleeve (93) of the transplanter (19).

10. A device as claimed in claim 9, wherein the sterile clamp cartridges (95) are contained in different angular orientations in a magazine pack (121) which can be inserted into the clamp cartridge changer (16).

11. A device as claimed in claim 10, wherein, coaxially to the transplanter (19) introduced into the changer, a rotatable and longitudinally displaceable gripper (123) is provided which grips and rotates the clamp cartridges (95), and wherein the latter are automatically fed to the gripper or ejected after use.

12. A device as claimed in claim 2, wherein the eyeball holder ring (14) is mounted on the auxiliary carrier (8) to be displaceable in the vertical direction (68) and to be precisely adjustable.

13. A device as claimed in claim 12, wherein the eyeball holder ring (14) is made of a transparent material and/or contains optical fibers (148, 149), for illuminating and observing the space within the ring.

14. A device as claimed in claim 1, wherein the axis adjustment instrument (17) is contructed as a monocular microscope with illumination (33) for observing the fundus of the eye and has a marking (40) in the center of the visual field, and wherein, behind and in front of the lens system (28), semi-reflecting mirrors (35, 36) are provided, by means of which a part of the beam is branched off and added back to the main optical path (30), this second optical path (37) running throught a second lens system (29).

15. A device as claimed in claim 14, wherein a video camera (42) which transmits the image received to a monitor (21) is provided on the axis adjustment instrument (17).

16. A device as claimed in claim 1, wherein the trephine (18) comprises a tubular cutter (52) and a holder (60) which is displaceable (50) relative to the carrier (11) in the axial direction of the tubular cutter and is precisely adjustable, and wherein a shaft (61) with, at its end, a suction pad (62) in the shape of the molding of gas-permeable design is fixed to the holder, which molding is connected through a longitudinal bore (64) in the shaft to a vacuum and has a contact surface (77) approximating the outer surface shape of the human cornea, and wherein the tubular cutter (52) is rotatably mounted to surround the shaft (61) and the suction pad (62) and is displaceable (59) relative to the holder (60) in the axial direction of the tubular cutter and is precisely adjustable, and wherein the tubular cutter (52) is insertable to fit into the eyeball holder ring (14).

17. A device as claimed in claim 11, wherein the axial mobility of the tubular cutter (52) is restricted between a position of readiness, retracted behind the contact surface (77) of the suction pad (62), and a pre-adjustable extreme cutting position.

18. A device as claimed in claim 16, wherein the tubular cutter (52) is driven by means of a motor.

19. A device as claimed in claim 16, wherein the tubular cutter (52) has, on its cutting edge, serrations (81) with ground cutting facets (82) which lead during the rotary movement.

20. A device as claimed in claim 16, wherein the suction pad (62) has a moisture-sensitive sensor (79) which reduces the vacuum applied and triggers a signal.

21. A device as claimed in claim 1, wherein the transplanter (19) comprises an elongate shaft (92) and a holder (90) which is rigidly joined thereto and which is adjustable (91) relative to the carrier (11) in the direction of the axis of the shaft (92) and is precisely adjustable, and wherein, at the end of the shaft, a suction pad (98, 99) is fitted which is connected through longitudinal bores (100, 101) in the shaft to a vacuum and has contact surfaces which approximate the outer surface shape of the human cornea, and wherein the suction pad has at least one clamp channel (111), ending in the contact surface, and a punch (104) for ejecting a clamp (113) contained in the clamp channel, the suction pad (98, 99) being insertable to fit into the eyeball holder ring (14).

22. A device as claimed in claim 21, wherein U-shaped clamps (113) are provided which have a connecting bridge and two parallel arms which carry inward-pointing barbs.

23. A device as claimed in claim 21, wherein V-shaped clamps (113a) are provided, the first arm of which is straight and pointed and the second arm of which is curved outwards corresponding to the curvature of the cornea surface and carries a barb at the end.

24. A device as claimed in claim 21, wherein V-shaped clamps (113b) are provided, the first arm of which has a circular outward curvature and is pointed, and the second arm of which is curved outwards corresponding to the curvature of the cornea surface and carries a barb at the end.

25. A device as claimed in claim 21, wherein the contact surface of the suction pad has an outer annular zone (99) and an inner zone (98) which are connected via separate lines (101 and 100) to individually adjustable vacuum sources.

26. A device as claimed in claim 25, wherein several clamp channels (111) are provided, the outlet orifices of which are arranged, in the region between the annular zone (99) and the inner zone (98), in a circle at equal spacings and with their length in the radial direction.

27. A device as claimed in claim 26, wherein the clamp channels (111) extend in the longitudinal direction of the shaft and the projecting punches (104) can be actuated together by means of an impact element (107, 94).

28. A device as claimed in claim 27, wherein the foot part of the shaft (92), the suction pad (98, 99) and the punches (104) form a clamp cartridge (95) which, by means of a quick-action coupling (96), can readily be taken off from the sleeve (93) and attached in different angular positions, as desired, the impact force being transmitted to the punches by means of a longitudinally movable impact sleeve (94).

* * * * *